US012649038B1

(12) United States Patent
Joshi et al.

(10) Patent No.: US 12,649,038 B1
(45) Date of Patent: Jun. 9, 2026

(54) OXYGEN DELIVERY APPARATUS

(71) Applicants: Shailendra Joshi, Ho Ho Kus, NJ (US); Vidur Joshi, Ho Ho Kus, NJ (US)

(72) Inventors: Shailendra Joshi, Ho Ho Kus, NJ (US); Vidur Joshi, Ho Ho Kus, NJ (US)

( * ) Notice: Subject to any disclaimer, the term of this patent is extended or adjusted under 35 U.S.C. 154(b) by 592 days.

(21) Appl. No.: 18/213,997

(22) Filed: Jun. 26, 2023

(51) Int. Cl.
 *A61M 16/06* (2006.01)
 *A61M 16/08* (2006.01)
(52) U.S. Cl.
 CPC .... *A61M 16/0616* (2014.02); *A61M 16/0683* (2013.01); *A61M 16/085* (2014.02); *A61M 2202/0208* (2013.01)
(58) Field of Classification Search
 CPC .......... A61M 16/0616; A61M 16/0683; A61M 16/085; A61M 2202/0208; A61M 16/06; A61M 16/0078; A61M 16/08; A61M 16/127; A61M 16/12; A61M 16/125; A62B 18/003; A62B 7/04
 See application file for complete search history.

(56) References Cited

U.S. PATENT DOCUMENTS

| | | | | |
|---|---|---|---|---|
| 3,850,171 A | * | 11/1974 | Ball ...................... | A61M 16/06 |
| | | | | 128/204.25 |
| 3,856,051 A | * | 12/1974 | Bain ................... | A61M 16/009 |
| | | | | 128/203.12 |
| 3,977,432 A | * | 8/1976 | Vidal ................. | A61M 16/127 |
| | | | | 137/893 |
| 4,281,652 A | * | 8/1981 | Miller .................. | A61M 16/08 |
| | | | | 128/911 |
| 2005/0028811 A1 | * | 2/2005 | Nelson ................ | A61M 16/107 |
| | | | | 128/200.11 |
| 2007/0283962 A1 | * | 12/2007 | Doshi ................. | A61M 16/106 |
| | | | | 128/206.18 |

* cited by examiner

*Primary Examiner* — Victoria Murphy
(74) *Attorney, Agent, or Firm* — Gulf Coast Intellectual Property Group

(57) ABSTRACT
An oxygen delivery apparatus operable to provide oxygen to a user wherein the invention includes a low volume mask body sealably secured over a user's mouth and nose. A gas source is operably coupled to the mask body with a first delivery tube. The first delivery tube has a portion thereof disposed within a second delivery tube. The delivery tubes are operably coupled to an inspiratory valve distal to the gas source. The inspiratory valve is operably coupled to the mask body providing gas flow thereinto in response to a user's inhalation. The mask includes a perimeter seal and employs a strap configuration to sealably secure the mask body to the face of the user. Integrally formed into the mask body are a plurality of expiratory valves. The expiratory valves are comprised of three layers and move between a closed position and an open position along the rearward perimeter edge.

12 Claims, 4 Drawing Sheets

OXYGEN DELIVERY APPARATUS

FIELD OF THE INVENTION

The present invention relates generally to breathing apparatus, more specifically but not by way of limitation, an oxygen delivery apparatus to be worn by a user on the face wherein the present invention provides a low volume mask capable of increased oxygen delivery efficiency. Furthermore, the present invention provides unique expiratory valves on the mask as well as a first delivery tube and a second delivery tube.

BACKGROUND

Oxygen therapy, also referred to as supplemental oxygen, is often utilized on people with COPD, emphysema, sleep apnea and other breathing problems to receive more oxygen so as to improve overall body function and fitness. Low blood oxygen levels can result in damage to organs and some individuals may require oxygen therapy for a short duration while those with chronic issues may employ supplemental oxygen for long durations. There are many commercially available oxygen machines and portable oxygen bottles that can be utilized by individuals to deliver oxygen. Most of the oxygen systems utilize a facemask that is donned by the user wherein the facemask delivers the oxygen to be inhaled by the user.

Conventional facemasks and oxygen delivery masks have inherent inefficiencies and flaws. One issue with conventional oxygen delivery systems is the volume of the facemasks. Most facemasks have a high volume that results in inefficiencies due to mixing of gases. Additionally, conventional facemasks do not employ optimized sealing and valves which results in inefficiencies due to leakage, backflow and dilution of oxygen. The combination of the material of the facemasks in conjunction with ineffective securing straps and anchoring points results in oxygen loss at the perimeter seal of the facemask. Lastly, conventional oxygen facemasks utilize only a single oxygen delivery tube which can limit the volume of oxygen supplied to the user and further can create complications should the source of oxygen de depleted.

Accordingly, there is a need for an oxygen delivery apparatus that is operable to provide oxygen flow to a user wherein the present invention includes a first delivery tube and a second delivery tube, that can serve as a reservoir for containing oxygen and further employs a facemask having a low volume creating increased efficiency.

SUMMARY OF THE INVENTION

It is the object of the present invention to provide an oxygen delivery apparatus configured to be operably coupled to an oxygen source wherein the present invention includes a facemask having broad strap members configured to secure the facemask to a user for optimal sealing to a user's face and prevention of leaks. Furthermore, the facemask is manufactured from a pliable material that is pulled onto the face by the strap members reducing the mask interior volume and improving seal against the user's face.

Another object of the present invention is to provide an oxygen delivery apparatus configured to provide an improved efficiency of the delivery of oxygen to a user wherein the present invention includes a first delivery tube and a second delivery tube. The first tube delivers the oxygen to the air inlet of the facemask and into the end of the larger second tube proximate thereto wherein a unidirectional flow valve allows oxygen enriched air in the second tube to enter into the facemask during inspiration.

A further object of the present invention is to provide an oxygen delivery apparatus configured to be operably coupled to an oxygen source wherein the first delivery tube is disposed within the second delivery tube and wherein the second delivery tube has an end open to atmospheric air ensuring that there is always breathable air even during loss of oxygen flow.

Yet a further object of the present invention is to provide an oxygen delivery apparatus configured to provide an improved efficiency of the delivery of oxygen to a user wherein the facemask employs expiratory flap valves formed on opposing sides thereof.

Still another object of the present invention is to provide an oxygen delivery apparatus configured to be operably coupled to an oxygen source wherein the straps secured to the facemask apply a distributed pressure on the perimeter seal of the facemask. The facemask is manufactured of a soft pliable material wherein the straps are applied distally from the edges of the facemask in order to pull the facemask onto the face of the user and inhibit leakage around the perimeter edge thereof.

An additional object of the present invention is to provide an oxygen delivery apparatus configured to provide an improved efficiency of the delivery of oxygen to a user wherein the first delivery tube and second delivery tube are operably coupled at a first end to an inspiratory valve.

Yet a further object of the present invention is to provide an oxygen delivery apparatus configured to be operably coupled to an oxygen source wherein the expiratory valves incorporated into the facemask are slit-like in formation and parallel to each other in configuration.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

DETAILED DESCRIPTION

Figure 1:
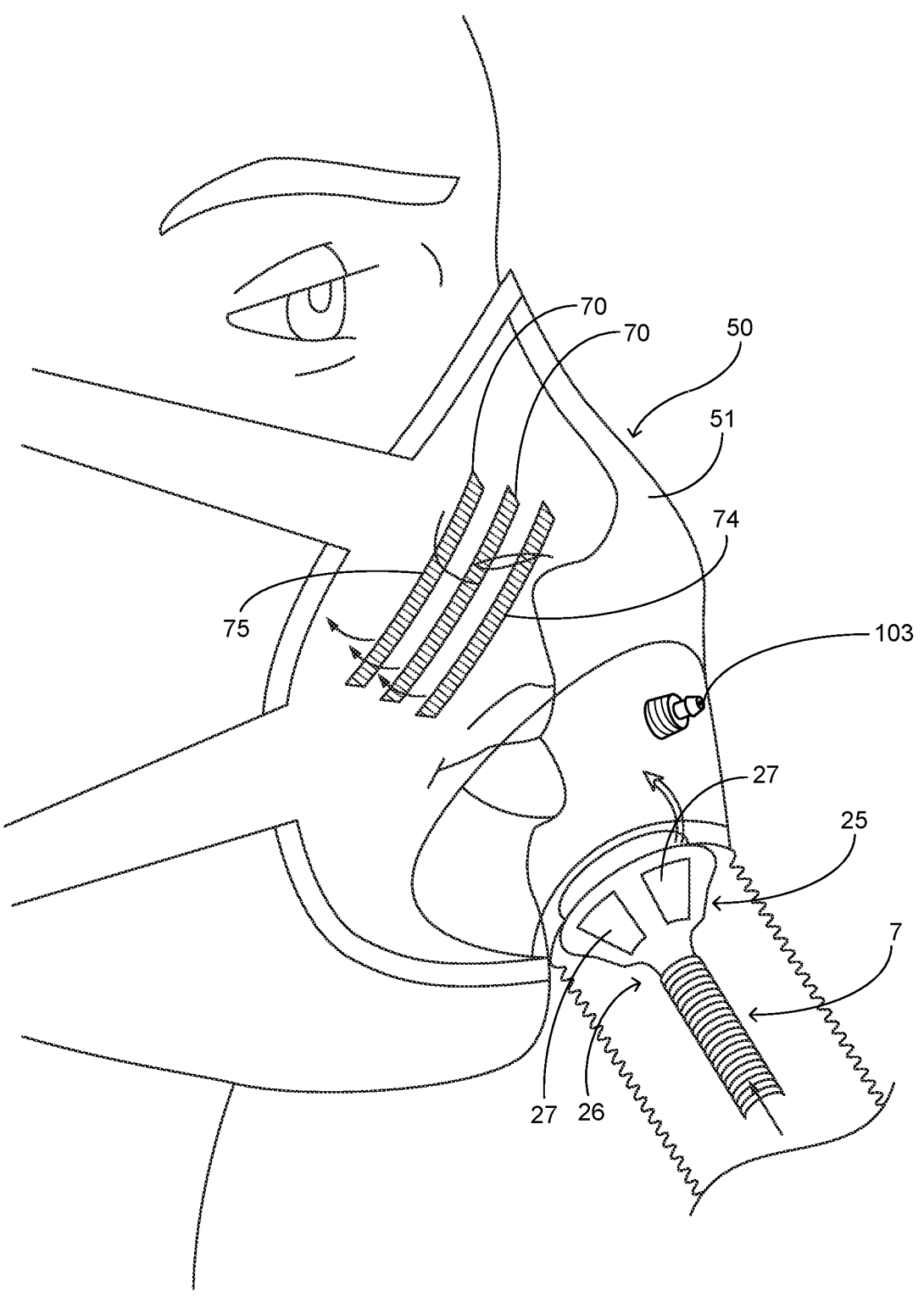
FIG. 1 is a side perspective view of an embodiment of the present invention.
Figure 2:
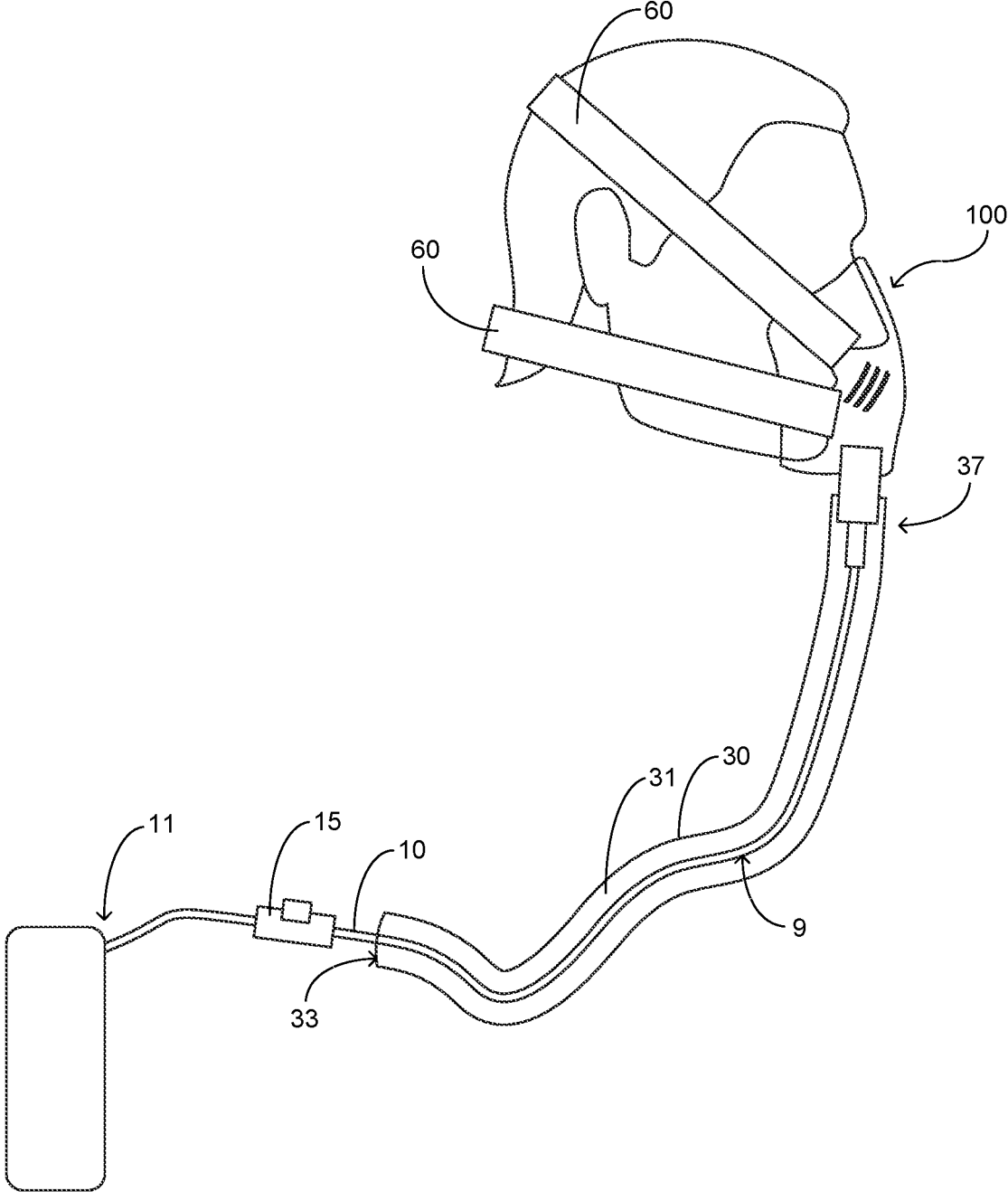
FIG. 2 is a perspective view of the present invention operably coupled to an oxygen source.
Figures 3, 4:
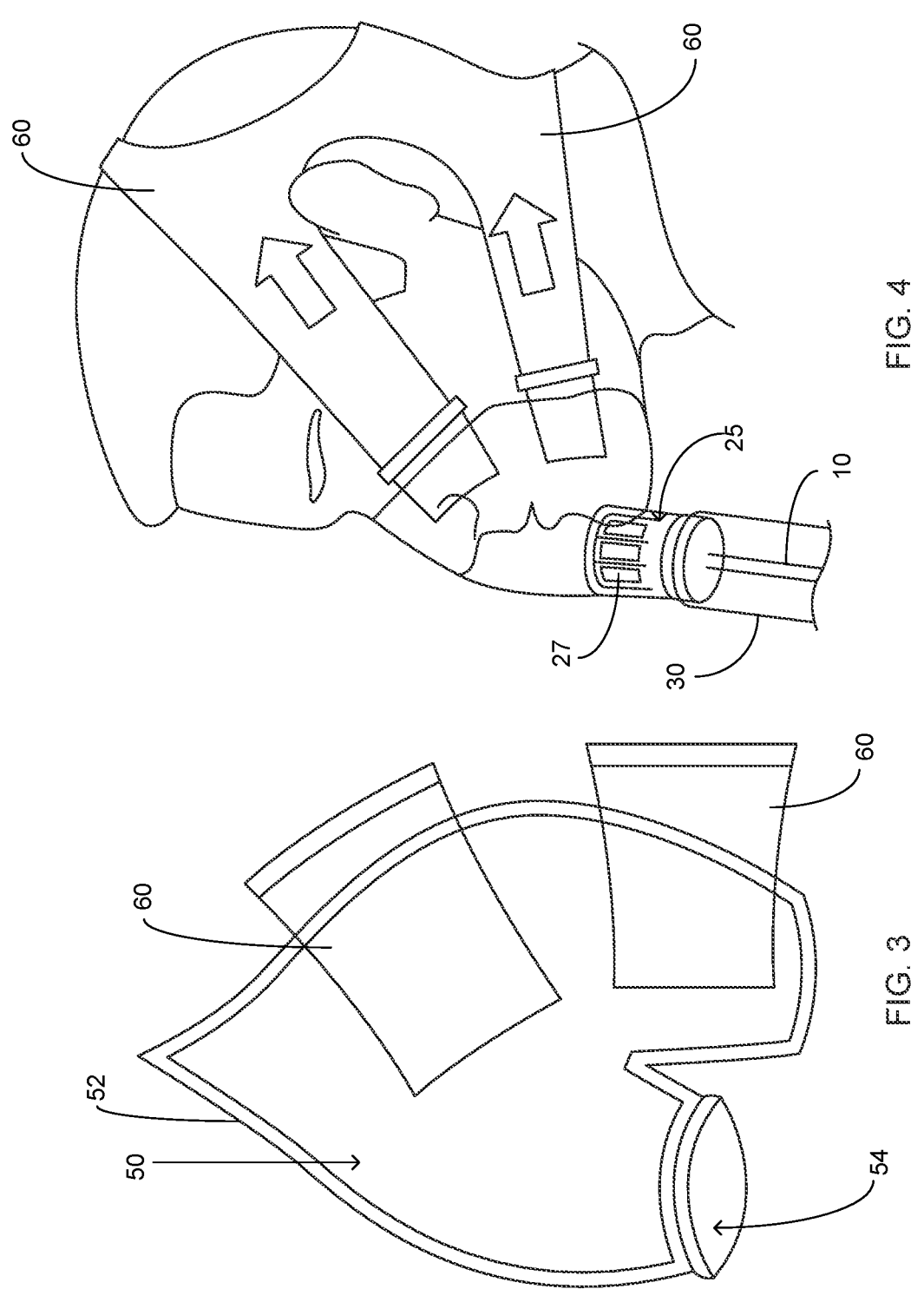
FIG. 3 is a side view of a portion of the facemask of the present invention.
FIG. 4 is a side view of the facemask with securing straps.
Figures 5, 6, 7:
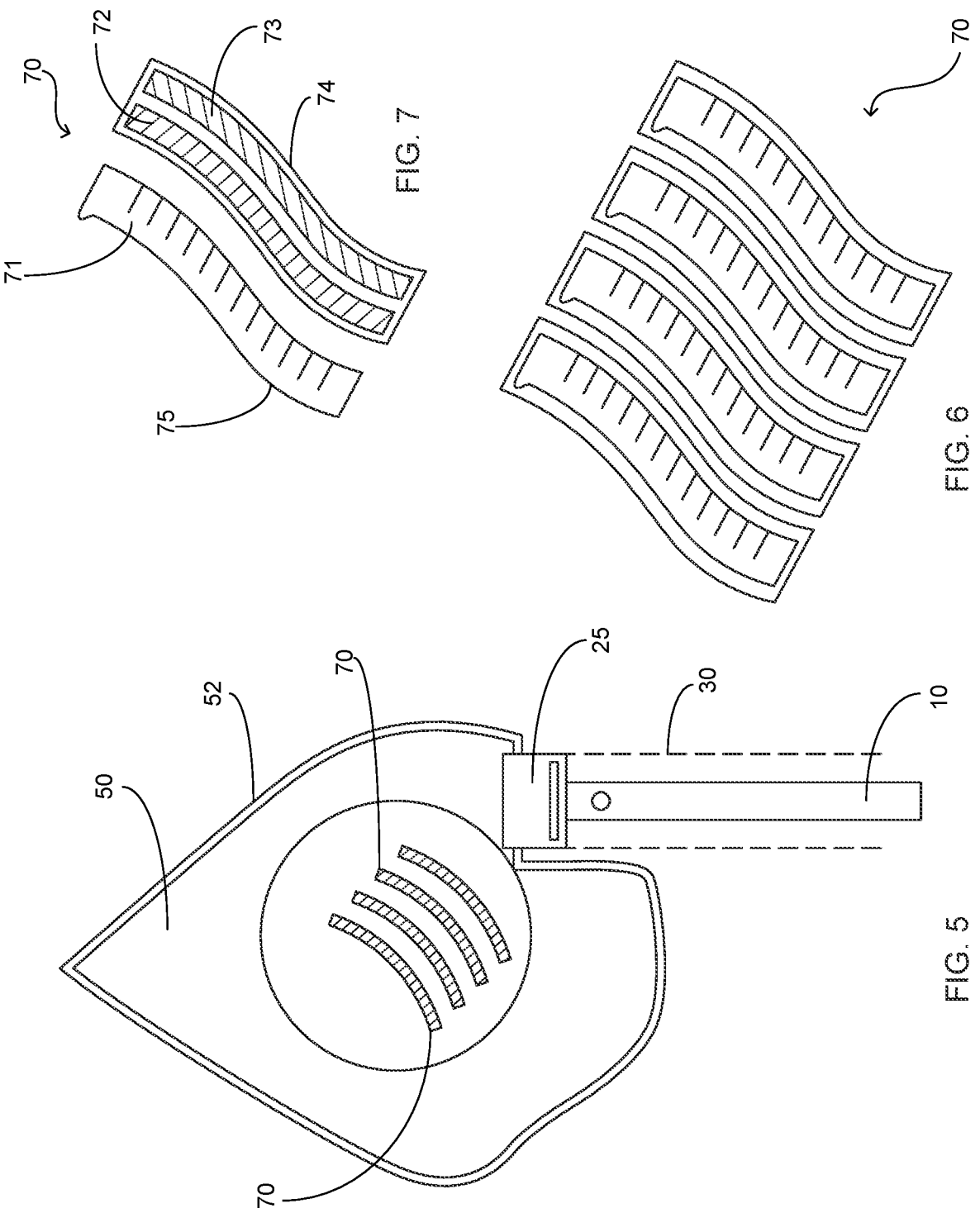
FIG. 5 is a detailed view of a portion of the facemask with expiratory valves.
FIG. 6 is a detailed view of a plurality of expiratory valves.
FIG. 7 is a detailed view of a single expiratory valve showing the layers thereof.

Referring now to the drawings submitted herewith, wherein various elements depicted therein are not necessarily drawn to scale and wherein through the views and figures like elements are referenced with identical reference numerals, there is illustrated an oxygen delivery apparatus 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to the Figures submitted herewith, the oxygen delivery apparatus 100 is configured to be operably coupled to a gas source 99. It should be understood within the scope of the present invention that the gas source 99 could be alternate sizes of a compressed oxygen bottles or a portable oxygen concentrator. The first delivery tube 10 is operably coupled to the gas source 99 proximate the first end 11 thereof. The first delivery tub 10 is manufactured from plastic tubing material and in a preferred embodiment has an internal diameter of eight millimeters. While the first delivery tube 10 can be provided in alternate lengths, it is contemplated within the scope of the present invention that the first delivery tube 10 is approximately one to one and a half meters in length. The first delivery tube 10 has operably coupled thereto a flow controller 15 wherein the flow controller 15 is proximate the first end 11 of the first delivery tube 10. The flow controller 15 is configured to provide operable control of the flow rate of oxygen delivered into the first delivery tube 10. It should be understood within the scope of the present invention that alternate types of conventional flow controllers could be employed. Furthermore, it is desired within the scope of the present invention that the flow controller 15 further include an ability to measure and display the flow rate of the oxygen into the first delivery tube 10.

The first delivery tube 10 includes second end 12 wherein the second end 12 is operably coupled to inspiratory valve 25. The first delivery tube 10 has a portion 9 thereof that is disposed within the interior volume of the second delivery tube 30. The second delivery tube 30 is manufactured from flexible plastic tubing material and includes hollow passage 31. The second delivery tube 30 in a preferred embodiment is approximately one meter in length having an internal diameter of twenty-two millimeters. In a preferred embodiment of the second delivery tube 30, the second delivery tube 30 has an interior volume of approximately five hundred milliliters. The second delivery tube 30 includes first end 33. First end 33 includes an opening providing access to and entry of atmospheric air. The opening at the first end 33 facilitates the presence of atmospheric air within the passage 31 of the second delivery tube 30. The volume of air available within the passage 31 of the second delivery tube 30 provides two benefits. First, if a user implements a larger than normal inhalation, the air within the second delivery tube 30 provides the additionally required volume of air. Secondly, upon depletion of the gas source 99, the volume of air within the passage 31 of the second delivery tube 30 as well as the opening at the first end thereof provides a supply of air so that the user of the oxygen delivery apparatus 100 can continue to breathe.

The second end 37 of the second delivery tube 30 and the second end 7 of the first delivery tube 10 are operably coupled to the inspiratory valve 25. The inspiratory valve 25 is a one-way valve that permits the flow of oxygen/air into the mask body 50 and is coupled to mask body 50 at opening 54 while inhibiting exhaled air from passing therethrough. In a preferred embodiment the inspiratory valve 25 employs flap members that are operable to move from a closed position to an open position when a user executes an inhalation. The bottom end 26 of the inspiratory valve 25 is operably coupled to second end 7 of the first delivery tube 10 and receives therefrom oxygen. The inspiratory valve 25 further includes ports 27 wherein ports 27 are operably coupled to the second delivery tube 30 and allow air contained therein to be transferred from the passage 31 through the inspiratory valve and into the mask body 50. As previously discussed herein, the volume of air contained in the passage 31 of the second delivery tube 30 is provided upon a user of the oxygen delivery apparatus 100 executing a large inhalation that exceeds the volume of the delivery capabilities of the first delivery tube 10. It is contemplated within the scope of the present invention that the inspiratory valve 25 could have alternate quantities of ports 27.

The mask body 50 is of suitable size to cover both the mouth and nose of a user. The mask body 50 is manufactured from a pliable material such as but not limited to plastic. The mask body 50 is configured so as to create a low internal volume in void 51 that exists between the face of the user and the mask body 50. The low volume present in the void 51 is configured to have a volume of less than forty milliliters. The volume of the second delivery tube 30 provides an inspiratory reservoir of five hundred to six hundred milliliters of oxygen enriched air. This volume is generally equivalent to an inhalation of a human. Ensuring the volume of the void 51 has volume that is equivalent to an average inhalation promotes efficiency of oxygen utilization as minimal excess oxygen is present and as such a maximum extraction of oxygen from the gas source 99 can be attained. The mask body 50 includes perimeter seal 52 wherein perimeter seal 52 is manufactured from a material such as but not limited to silicone rubber. The perimeter seal 52 functions to hermetically seal the void 51 from the atmosphere. Strap members 60 provide anchoring of the mask body 50 in at least two different locations and angles so as to ensure bias of the perimeter seal 52 against the face of the user. Strap members 60 are manufactured from nylon or other similar material and are operably coupled to the mask body 50 utilizing suitable techniques. It should be understood within the scope of the present invention that the strap members 60 could be provided in various alternate configuration wherein each configuration has at least two different anchoring points on the head of the user. It should be further understood within the scope of the present invention that the strap members 60 are adjustable. The mask body 50 is further equipped with a gas sampling port 103 wherein the gas sampling port 103 can be configured with a Luer-Lock or other mechanism to operably couple to an element configured to retrieve a gas sample.

The mask body 50 has formed therein a plurality of expiratory valves 70. The expiratory valves 70 are formed on both sides of the mask body 50 and function to permit release of exhaled air from the void 51. The expiratory valves 70 are manufactured from a soft pliable material such as but not limited to silicone rubber. The expiratory valves 70 include a first layer 71, second layer 72 and third layer 73. The expiratory valves 70 are secured to the mask body 50 along a forward perimeter edge 74. The rearward perimeter edge 75 lays against the mask body 50 and is configured to move outwards from the mask body 50 as a result of air pressure from an exhalation from the user. Upon being moved to its second position, the rearward perimeter edge 75 is no longer biased against the mask body 50 and as such air escapes the void 51. In the first position of the expiratory valve 70, the rearward perimeter edge 75 is biased against the mask body 50. The three layers and material of the expiratory valve 70 enable a flap-like movement wherein the expiratory valve 70 moves between a first position and a second position wherein in the second position exhaled air escapes the void 51 of the mask body 50. While three and four expiratory valves 70 are illustrated on the sides of the mask body 50 herein, it is contemplated within the scope of the present invention that the mask body 50 could have more or less than three expiratory valves 70 on each side thereof. The material of the expiratory valves 70 further allows the rearward perimeter edge 75 to sealably rest on the mask body 50 and seal the void 51 so as to accommodate the contoured shape of the mask body 50.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. An oxygen delivery apparatus configured to provide efficient utilization of oxygen from a gas source wherein the oxygen delivery apparatus comprises:

a mask body, said mask body configured to cover a mouth and a nose of a user, said mask body having a perimeter edge, said perimeter edge configured to be sealably secured to a face of the user, said mask body configured to create a void between an inner surface thereof and the face of the user;

a plurality of expiratory valves, said plurality of expiratory valves being elongated and rectangular in form, said plurality of expiratory valves being formed in opposing sides of said mask body, said plurality of expiratory valves configured to move between a closed position and an open position upon exhalation of the user, said plurality of expiratory valves configured to open along a rearward perimeter edge;

an inspiratory valve, said inspiratory valve being operably coupled to said mask body;

a first delivery tube, said first delivery tube having a first end and a second end, said second end of said first delivery tube being directly coupled to said inspiratory valve, said first end of said first delivery tube being operably coupled to the gas source, said first delivery tube having a portion thereof disposed within a second delivery tube, said second delivery tube having a first end and a second end, said second end of said second delivery tube being operably coupled to said inspiratory valve;

wherein said first end of said second delivery tube has an opening, said opening of said first end of said second delivery tube being open to atmospheric air.

2. The oxygen delivery apparatus configured to provide efficient utilization of oxygen from a gas source as recited in claim 1, wherein said inspiratory valve further includes a plurality of ports, said plurality of ports being operably coupled to said first delivery tube and said second delivery tube allowing gas to flow inward therefrom into the void.

3. The oxygen delivery apparatus configured to provide efficient utilization of oxygen from a gas source as recited in claim 2, wherein said mask body has operably coupled thereto strap members, said strap members configured to secure said mask body to at least two different locations on a head of the user.

4. The oxygen delivery apparatus configured to provide efficient utilization of oxygen from a gas source as recited in claim 3, wherein said plurality of expiratory valves include a first layer, a second layer and a third layer.

5. The oxygen delivery apparatus configured to provide efficient utilization of oxygen from a gas source as recited in claim 4, wherein said plurality of expiratory valves are sealed to said mask body along a forward perimeter edge.

6. The oxygen delivery apparatus configured to provide efficient utilization of oxygen from a gas source as recited in claim 5, wherein the second delivery tube includes a passage having a capacity to retain approximately 500 milliliters of atmospheric air.

7. The oxygen delivery apparatus configured to provide efficient utilization of oxygen from a gas source as recited in claim 6, and further including a flow controller, said flow controller being operably coupled to said first delivery tube, said flow controller configured to provide control of a gas flow from the gas source into said first delivery tube.

8. An oxygen delivery apparatus operable to provide oxygen from a gas source to a user wherein the oxygen delivery apparatus comprises:

a first delivery tube, said first delivery tube having a first end and a second end, said first end being operably coupled to the gas source, said first delivery tube being hollow to facilitate flow of oxygen therethrough;

a second delivery tube, said second delivery tube having a first end and a second end, said first end having an opening providing access to a hollow passage of the second delivery tube, said second delivery tube having a diameter that is greater than a diameter of the first delivery tube, said second delivery tube have a portion of the first delivery tube disposed therein;

an inspiratory valve, said inspiratory valve being a one-way valve, said second end of said first delivery tube being operably coupled to said inspiratory valve, said second end of said second delivery tube being operably coupled to said inspiratory valve, wherein gas from said first delivery tube and said second delivery tube pass through said inspiratory valve upon inhalation by the user of the oxygen delivery apparatus, a mask body, said mask body configured to cover a mouth and a nose of a user, said inspiratory valve being operably coupled to said mask body, said mask body having a perimeter edge, said perimeter edge configured to be sealably secured to a face of the user, said mask body configured to create a void between an inner surface thereof and the face of the user, said mask body having at least two strap members secured thereto, said at least two strap members configured to secure around a head of the user in two different locations; and a plurality of expiratory valves, said plurality of expiratory valves being elongated and rectangular in form, said plurality of expiratory valves being formed in opposing sides of said mask body, said plurality of expiratory valves configured to move between a closed position and an open position upon exhalation of the user, said plurality of expiratory valves configured to open along a rearward perimeter edge upon an exhalation by the user;

wherein said opening at said first end of said second delivery tube being open to atmospheric air.

9. The oxygen delivery apparatus operable to provide oxygen from a gas source to the user as recited in claim 8, wherein said plurality of expiratory valves are sealed to said mask body along a forward perimeter edge.

10. The oxygen delivery apparatus operable to provide oxygen from a gas source to the user as recited in claim 9, wherein said plurality of expiratory valves include a first layer, a second layer and a third layer.

11. The oxygen delivery apparatus operable to provide oxygen from a gas source to the user as recited in claim 10, wherein said inspiratory valve further includes a plurality of ports, said plurality of ports allowing gas to flow inward from said first delivery tube and said second delivery tube into the void.

12. The oxygen delivery apparatus operable to provide oxygen from a gas source to the user as recited in claim 11, wherein said plurality of ports of said inspiratory valve provide gas from said second delivery tube upon an inhalation exceeding a capacity supplied by said first delivery tube.

* * * * *